US010548567B2

(12) United States Patent
Huepf

(10) Patent No.: US 10,548,567 B2
(45) Date of Patent: Feb. 4, 2020

(54) SYSTEM AND METHOD FOR DISPLAYING MEDICAL IMAGES OF AN OBJECT WITHIN A PATIENT

(71) Applicant: GENERAL ELECTRIC COMPANY, Schenectady, NY (US)

(72) Inventor: Thomas Huepf, Zipf (AT)

(73) Assignee: GENERAL ELECTRIC COMPANY, Schenectady, NY (US)

(*) Notice: Subject to any disclaimer, the term of this patent is extended or adjusted under 35 U.S.C. 154(b) by 233 days.

(21) Appl. No.: 15/376,984

(22) Filed: Dec. 13, 2016

(65) Prior Publication Data

US 2018/0161008 A1    Jun. 14, 2018

(51) Int. Cl.
| | |
|---|---|
| *A61B 8/00* | (2006.01) |
| *H04N 5/232* | (2006.01) |
| *H04N 7/18* | (2006.01) |
| *G06T 11/60* | (2006.01) |
| *A61B 5/055* | (2006.01) |
| *A61B 6/00* | (2006.01) |
| *A61B 8/08* | (2006.01) |

(52) U.S. Cl.
CPC ............ *A61B 8/462* (2013.01); *A61B 8/0866* (2013.01); *G06T 11/60* (2013.01); *A61B 6/462* (2013.01); *H04N 7/183* (2013.01)

(58) Field of Classification Search
CPC ....... A61B 8/462; A61B 8/0866; A61B 5/055; A61B 6/462; H04N 5/23293; H04N 7/183; G06T 11/60
USPC .......................................................... 348/77
See application file for complete search history.

(56) References Cited

U.S. PATENT DOCUMENTS

| 9,113,817 | B2 | 8/2015 | Tripathi | |
|---|---|---|---|---|
| 2006/0152478 | A1* | 7/2006 | Simon | G05B 19/41875 345/156 |
| 2011/0154569 | A1* | 6/2011 | Wiggers | A61B 6/0407 5/81.1 R |
| 2014/0095637 | A1* | 4/2014 | Cropper | H04L 67/22 709/206 |
| 2014/0361957 | A1* | 12/2014 | Hua | G06F 3/013 345/8 |
| 2015/0038844 | A1* | 2/2015 | Blalock | A61B 8/4427 600/440 |

(Continued)

FOREIGN PATENT DOCUMENTS

WO    2003053247 A1    7/2003

*Primary Examiner* — Zaihan Jiang
(74) *Attorney, Agent, or Firm* — Grogan, Tuccillo & Vanderleeden, LLP

(57) ABSTRACT

A system for displaying medical images of an object within a patient is provided. The system includes: a medical imaging apparatus operative to generate the medical images of the object; and a mobile electronic device having a front side and a rear side and operative to electronically communicate with the medical imaging apparatus so as to receive the medical images from the medical imaging apparatus. The front side includes a display, and the rear side is opposite the front side and defines a line of sight that projects outwardly from the mobile electronic device. The mobile electronic device is further operative to move about the patient and show the medical images on the display such that the medical images depict a view of the object from the perspective of the mobile electronic device along the line of sight.

18 Claims, 4 Drawing Sheets

(56) References Cited

U.S. PATENT DOCUMENTS

| | | | |
|---|---|---|---|
| 2015/0244982 A1* | 8/2015 | Yang | H04L 65/1059 |
| | | | 348/14.07 |
| 2015/0264567 A1* | 9/2015 | Sensharma | H04W 12/06 |
| | | | 455/411 |
| 2015/0350545 A1* | 12/2015 | Welsh | A61B 6/4405 |
| | | | 348/77 |
| 2016/0135903 A1* | 5/2016 | Christian | G06T 7/0012 |
| | | | 382/103 |
| 2016/0139399 A1* | 5/2016 | O'Connell | G02B 25/002 |
| | | | 359/801 |
| 2016/0141809 A1* | 5/2016 | Choi | H01R 13/6683 |
| | | | 439/38 |
| 2016/0182596 A1* | 6/2016 | Ralph | H04L 65/608 |
| | | | 709/219 |
| 2016/0350649 A1* | 12/2016 | Zhang | G06N 3/0454 |
| 2017/0201285 A1* | 7/2017 | Liu | H04B 1/3888 |
| 2018/0108440 A1* | 4/2018 | Stevens | G16H 40/67 |

* cited by examiner

SYSTEM AND METHOD FOR DISPLAYING MEDICAL IMAGES OF AN OBJECT WITHIN A PATIENT

BACKGROUND

Technical Field

Embodiments of the invention relate generally to medical imaging technologies, and more specifically, to a system and method for displaying medical images of an object within a patient.

Discussion Of Art

Medical imaging systems provide for the ability to image objects within a patient, e.g., bones, organs, fluids, etc. For example, ultrasound imaging systems generate images of objects within a patient by transmitting sound waves into the patient and analyzing returned echoes and magnetic resonance imaging ("MRI") systems generate images of objects within a patient by placing a patient in a magnetic field, exciting atoms within the patient while in the magnetic field, and analyzing radio frequencies emitted by the atoms as they relax back to lower energy states.

Many medical imaging systems display generated medical images on screens having fixed positions. Such screens, however, are often not easily viewed by the patient undergoing the imaging procedure, e.g., a fetal ultrasound. Further, the medical images displayed on such screens are typically from a fixed perspective. As such, many medical imaging systems do not provide for a person to dynamically define the perspective of the medical images in real-time. In other words, in many medical imaging systems, the perspective of the medical images remains the same as a person viewing the images moves around the patient.

What is needed, therefore, is an improved system and method for displaying medical images of an object within a patient.

BRIEF DESCRIPTION

In an embodiment, a system for displaying medical images of an object within a patient is provided. The system includes: a medical imaging apparatus operative to generate the medical images of the object; and a mobile electronic device having a front side and a rear side and operative to electronically communicate with the medical imaging apparatus so as to receive the medical images from the medical imaging apparatus. The front side includes a display, and the rear side is opposite the front side and defines a line of sight that projects outwardly from the mobile electronic device. The mobile electronic device is further operative to move about the patient and show the medical images on the display such that the medical images depict a view of the object from the perspective of the mobile electronic device along the line of sight.

In another embodiment, a method for displaying medical images of an object within a patient is provided. The method includes: moving a mobile electronic device about the patient, the mobile electronic device having a front side and a rear side opposite the front side, the front side including a display and the rear side defining a line of sight that projects outwardly from the mobile electronic device; generating the medical images via a medical imaging apparatus in electronic communication with the mobile electronic device; transmitting the medical images to the mobile electronic device via the medical imaging apparatus; and displaying the medical images on the mobile electronic device such that the medical images depict a view of the object from the perspective of the mobile electronic device along the line of sight.

In yet another embodiment, a non-transitory computer readable medium is provided. The non-transitory computer readable medium stores instructions configured to adapt a mobile electronic device to: transmit at least one of device position data and device orientation data to a medical imaging apparatus operative to generate medical images of an object within a patient; receive the medical images from the medical imaging apparatus; and show the medical images on a display on a front side of the mobile electronic device such that the medical images depict a view of the object from the perspective of the mobile electronic device along a line of sight extending outwardly from the mobile electronic device from a rear side of the mobile electronic device opposite the front side.

DRAWINGS

The present invention will be better understood from reading the following description of non-limiting embodiments, with reference to the attached drawings, wherein below:

DETAILED DESCRIPTION

Figure 1:
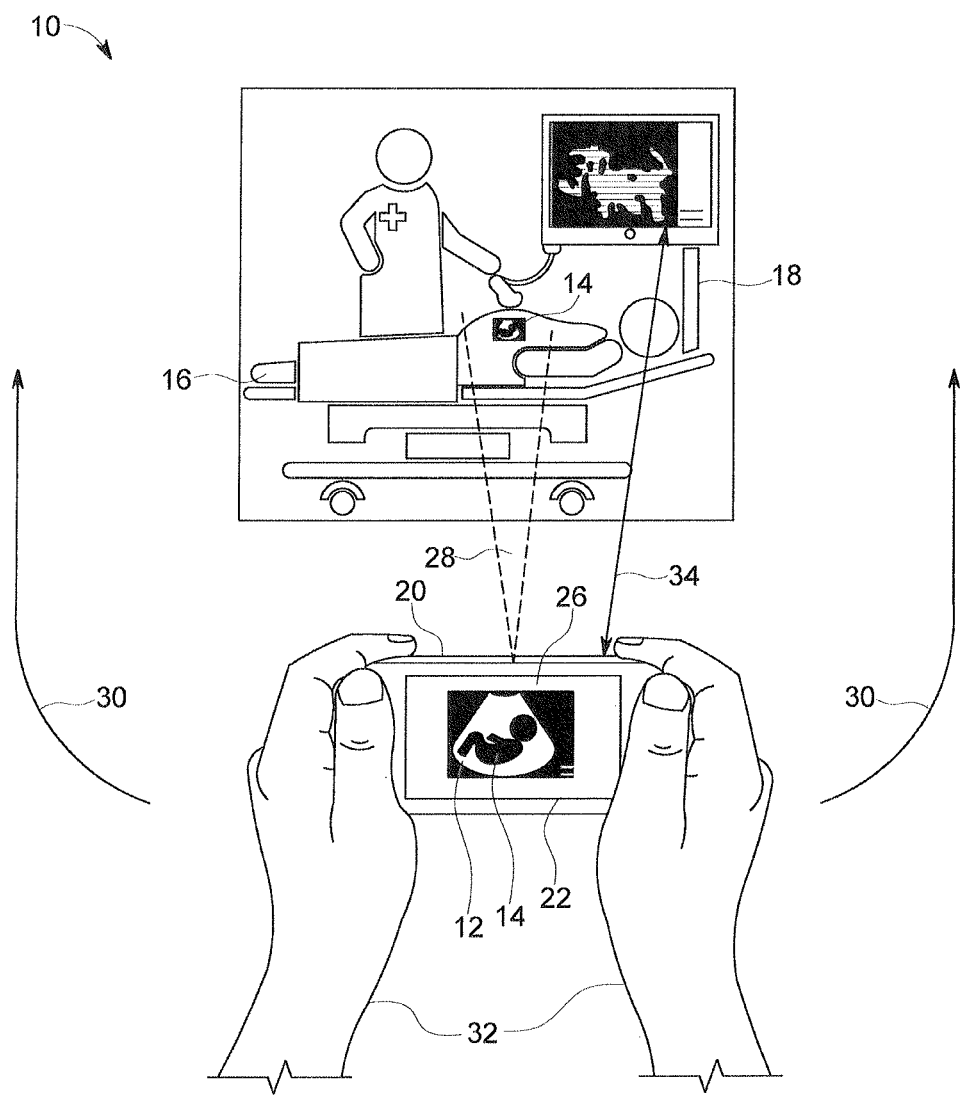
FIG. 1 is a diagram of a system for displaying medical images of an object within a patient in accordance with an embodiment of the present invention.

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. The term "real-time," as used herein, means a level of processing responsiveness that a user senses as sufficiently immediate or that enables the processor to keep up with an external process.

Further, while the embodiments disclosed herein are described with respect to ultrasound systems and images, it is to be understood that embodiments of the present invention may be applicable to other types of imaging systems capable of visualizing an object within another object, e.g., MRIs, X-ray imaging systems, etc. Further still, as will be appreciated, embodiments of the present invention related imaging systems may be used to analyze tissue generally and are not limited to human tissue.

Referring now to FIG. 1, the major components of a system 10 for displaying medical images 12 of an object 14, e.g., a fetus, organ, blood flow, bone, etc., according to an embodiment of the invention are shown. The system includes a medical imaging apparatus 18 operative to generate the medical images 12 of the object 14, which in embodiments may be two-dimensional ("2D") and/or three-dimensional ("3D"), and a mobile electronic device 20 having a front side 22 and a rear side 24 (FIGS. 2 and 3) and operative to electronically communicate with the medical imaging apparatus 18 so as to receive the medical images 12 from the medical imaging apparatus 18. The front side 22 includes a display 26, and the rear side 24 is opposite of the front side 22 and defines a line of sight 28 that projects outwardly from the mobile electronic device 20.

As used herein, the term "line of sight" refers to a region of space that projects outwardly from an object that encompasses all, or part of, one or more objects, e.g., the line of sight extending from the lens of a camera or the eyes of a person. The mobile electronic device 20 is further operative to move about, as represented by arrows 30, the patient 16 and show the medical images 12 on the display 26 such that the medical images 12 depict a view of the object 14 from the perspective of the mobile electronic device 20 along the line of sight 28. In other words, as an operator 32 of the mobile electronic device 20 moves the mobile electronic device 20 about the patient 16, e.g., above, below, to the left, and/or to the right, the medical images 12 shown on the display 26 depict the object 14, which is normally not visible to the operator 32 as the patient's 16 body typically blocks the object 14 from view. Thus, in embodiments wherein the operator 32 holds the mobile electronic device 20 such that the line of sight 28 of the mobile electronic device 20 is aligned with, or close to, the operator's 32 line of sight, e.g., aligned with the operator's eyes, the display 26 operates as a virtual window that allows the operator 32 to "see-through" the patient's 16 body and view the object 14. As will be appreciated, in embodiments, the operator 32 may not be a physician, or other medical professional, tending to the object/patient 16, but rather a friend and/or relative of the patient 16 and/or of the object/fetus 14, e.g., the father of the fetus 14. In embodiments, the operator 32 may be a physician and/or other medical professional tending to the object/patient 16.

As stated above, the medical imaging apparatus 18 generates the medical images 12. As will be appreciated, in embodiments, the medical imaging apparatus 18 may be any type of medical imaging system capable of imaging an object within another object, e.g., a magnetic resonance imaging device, an ultrasound imaging device, an x-ray imaging device, etc.

As also stated above, the mobile electronic device 20 is in electronic communication with the imaging apparatus 18 and shows/displays the medical images 12 on the display 26. As will be appreciated, the mobile electronic device 20 may be any type of mobile electronic device to include cell/smart phones, tablets, laptops, smart glasses, virtually reality ("VR") headsets, etc, which have at least one processor, a memory device, and a display 26. As will be further appreciated, the mobile electronic device 20 receives the medical images 12 from the medical imaging apparatus 18 via an electronic connection 34. In embodiments, the electronic connection 34 may be wireless, e.g., WiFi, Bluetooth, or other appropriate wireless protocol. In other embodiments, the electronic connection 34 may be a wired connection, e.g., USB, Firewire, Ethernet, or other appropriate protocols.

Figure 2:
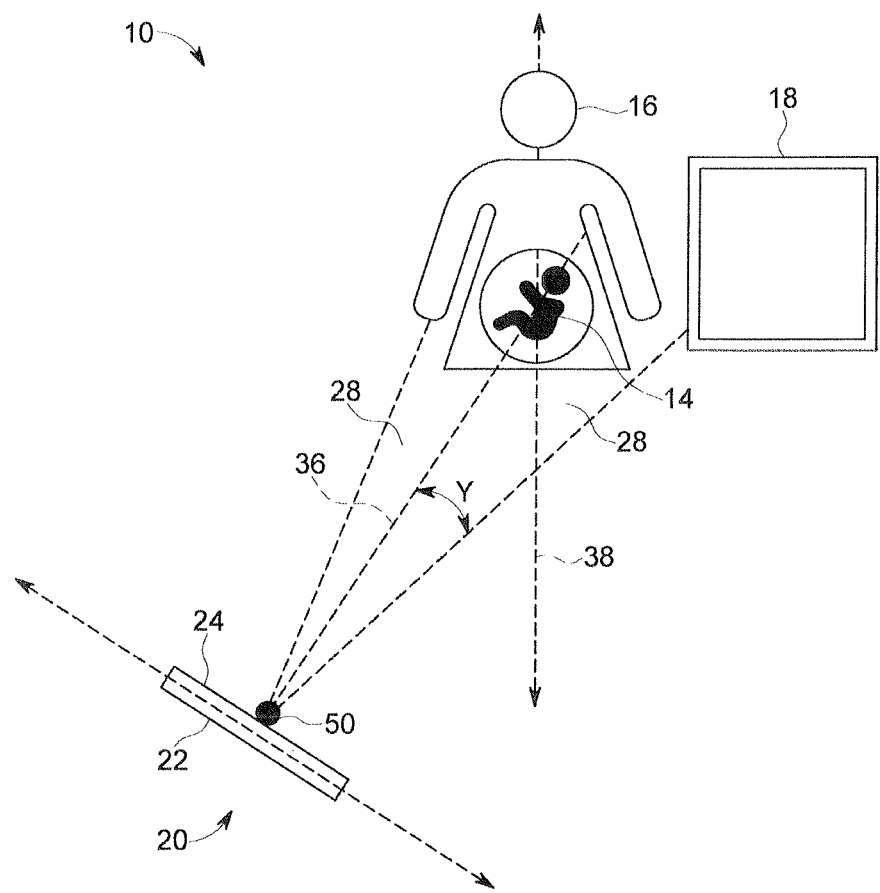
FIG. 2 is another diagram of the system of FIG. 1 depicting a top-down view of the system in accordance with an embodiment of the present invention.
Figure 3:
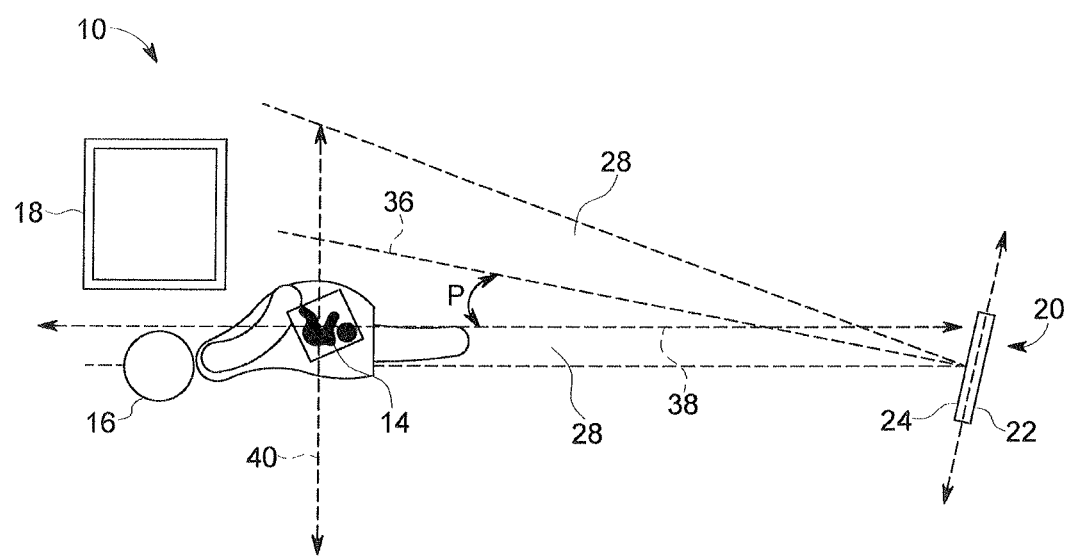
FIG. 3 is yet another diagram of the system of FIG. 1 depicting a side view of the system in accordance with an embodiment of the present invention.

Turning now to FIGS. 2 and 3, in certain embodiments, the mobile electronic device 20 may transmit, via electronic connection 34, device orientation data to the medical imaging apparatus 18, and the medical imaging apparatus 18 generates the medical images 12 based at least in part on the device orientation data. As will be understood, in embodiments, the device orientation data may convey/describe the yaw and/or pitch of the mobile electronic device 20. As shown in FIG. 2, the yaw of the mobile electronic device 20 is the angle Y that a line 36 normal to the rear side 24 of the mobile electronic device 20 makes with a horizontal axis 38 of the patient 16 in a plane horizontal to the patient 16. As shown in FIG. 3, the pitch of the mobile electronic device 20 is the angle P that the line 36 normal to the rear side 24 of the mobile electronic device 20 makes with the horizontal axis 38 in a plane defined by the horizontal axis 38 and a vertical axis 40 of the patient 16.

As will be appreciated, the mobile electronic device 20 may generate the orientation data via one or more internal sensors, e.g., accelerometers. In other embodiments, the orientation data may be generated via one or more sensors external to the mobile electronic device 20, e.g., cameras, magnetic sensors, etc.

Figure 4:
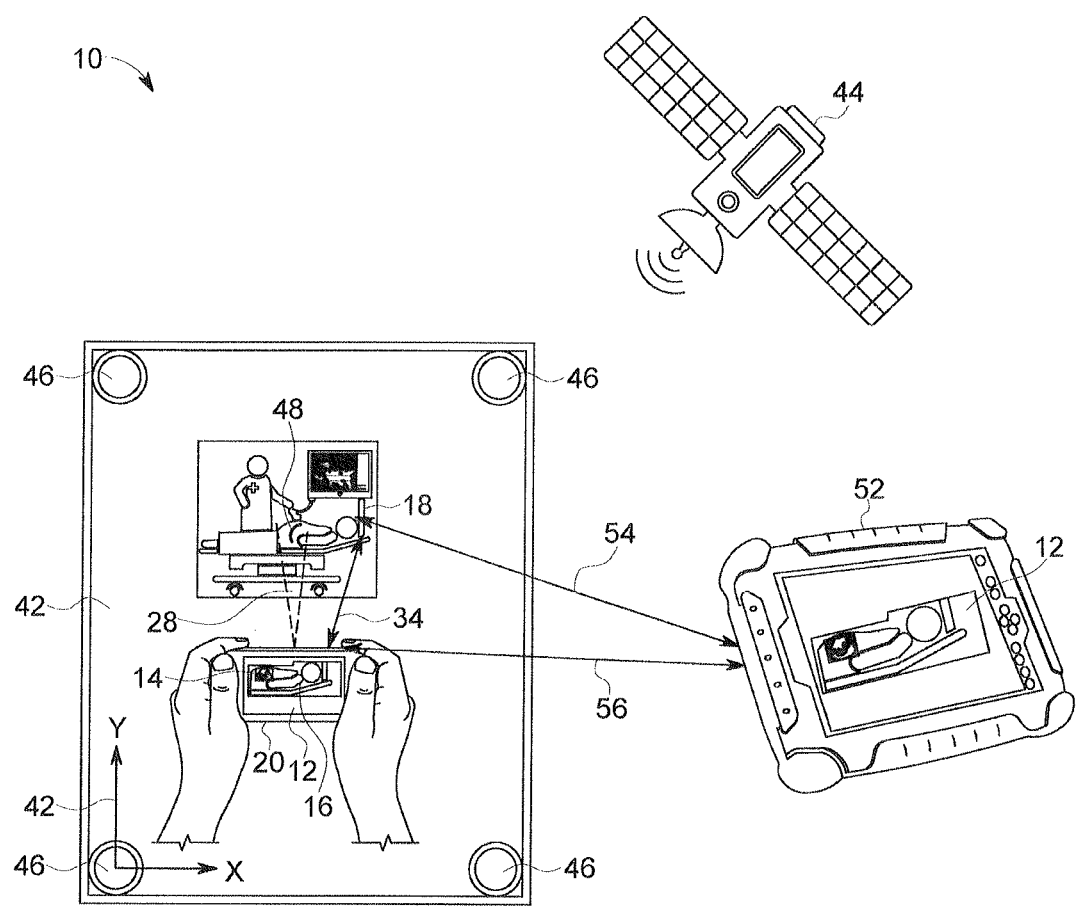
FIG. 4 is still yet another diagram of the system of FIG. 1 in accordance with an embodiment of the present invention.

As illustrated in FIG. 4, the mobile electronic device 20 may transmit, via electronic connection 34, device position data to the medical imaging apparatus 18, and the medical imaging apparatus 18 generates the medical images 12 based at least in part on the device position data. As will be understood, the device position data conveys/describes positional information about the mobile electronic device 20 to the medical imaging system 18.

For example, in embodiments, the device position data may convey/describe the location of the mobile electronic device 20 in relation to the medical imaging device 18. In such embodiments, the device position data may describe the position of the mobile electronic device 20 via a 2D and/or 3D radian and/or Cartesian coordinate system 42. In embodiments, the device position data may describe the position of the mobile electronic device 20 as a GPS 44 coordinate, i.e., the mobile electronic device 20 may include a GPS antenna.

As further illustrated in FIG. 4, in certain embodiments, the system 10 may further include one or more positioning beacons 46 that transmits positional reference data that may be received by the mobile electronic device 20. In such embodiments, the mobile electronic device 20 may generate the device position data based at least in part on the positional reference data. For example, the positional reference data may contain information data, e.g., coordinates, distances, and/or a timing signal, which allows the mobile electronic device 20 to derive/calculate its position with respect to the positioning beacons 46 and/or the medical imaging apparatus 18. Accordingly, the positioning beacons 46 may transmit the positional reference data via radio waves, to include WiFi, Bluetooth, and/or other appropriate wireless protocols. In aspects, the positioning beacons 46 may be disposed apart from the medical imaging apparatus 18. In embodiments, the positioning beacons 46 may be disposed near and/or integrated into the medical imaging apparatus 18.

Further, in certain embodiments, the system 10 may include one or more patient positional sensors 48 in electronic communication with the medical imaging apparatus 18 so as to transmit patient position data to the medical imaging apparatus 18. Accordingly, the medical imaging apparatus 18 generates the medical images 12 based at least in part on the patient position data. As will be understood, the patient position data may include data, e.g., GPS coordinates, distances, timing signals, etc., which allow the medical imaging apparatus 18 to determine and/or calculate the position of the patient 16 with respect to the mobile electronic device 20 and/or the medical imaging apparatus 18. In embodiments, the patient position data may provide for the medical imaging apparatus 18 to utilize the same coordinate system 42 for both the patient 16 and the mobile electronic device 20. Further, the patient positional sensors 48 may receive the positional reference data from the one or more positioning beacons 46 and generate the patient position data based at least in part on the positional reference data.

In embodiments, the patient positional sensors 48 transmit patient orientation data to the medical imaging apparatus 18. As will be understood, the patient orientation data may include data, e.g., angles, radians, etc., which allow the medical imaging apparatus 18 to determine and/or calculate an orientation of the patient 16. Accordingly, in embodiments, the medical imaging apparatus 18 generates the medical images 12 based at least in part on the patient orientation data.

As such, in embodiments, the patient positional sensors 48 include GPS antennas, WiFi/Bluetooth antennas, accelerometers, gyros, cameras, etc. The patient positional sensors 48 may be integrated into a mat, belt, harness, and/or other object worn by and/or draped over the patient 16.

Further, the rear side 24 of the mobile electronic device 20 may include a camera 50 (FIG. 2) oriented along the line of sight 28 and operative to generate images of the patient 16. In such embodiments, the mobile electronic device may be further operative to combine the images of the patient 16 with the medical images 12 such that the medical images 12 further depict an augmented reality view of the object 14 and the patient 16 as shown in FIG. 4. As will be understood, the augmented reality view combines objects from the images obtained by the camera with the medical images 12 generated by the medical imaging apparatus 18 so as to produce a hybrid image of the two image sets. For example, in embodiments wherein the medical imaging apparatus 18 is an ultrasound system and the object 14 is a fetus, the augmented reality view may be generated by overlaying and/or otherwise integrating images of the fetus obtained by the ultrasound system into images of the patient obtained/generated by the camera 50.

Additionally, the medical imaging apparatus 18 and/or the mobile electronic device 20 may broadcast/stream the medical images 12 to a remote electronic device 52 via electrical connections 54 and 56, respectively. As will be appreciated, in embodiments, the remote electronic device 52 may be a tablet, smart phone, laptop, smart television, and/or any other electronic device capable of displaying the medical images 12, and which is located apart from both the medical imaging apparatus 18 and the mobile electronic device 20. The electrical connections 54 and/or 56 may include a network connection, e.g., the Internet, and/or other another electronic communication system capable of transmitting the medical images 12.

Accordingly, the mobile electronic device 20 and/or the patient 16 may need to be registered with the medical imaging apparatus 18. As will be understood, the term "registering," as used herein, refers to the process of initially informing/transmitting position data and/or orientation data to the medical imaging apparatus 18. For example, in embodiments, mobile electronic device 20 may register with the medical imaging apparatus 18 by sending its initial device position data and/or device orientation data. Similarly, the patient 16 may register with the medical imaging apparatus 18 by adorning the patient positional sensors 48 which in turn inform/transmit the initial patient position data and/or patient orientation data to the medical imaging apparatus 18. In embodiments, the mobile electronic device 20 and/or the patient 16, via the patient positional sensors 48, may update/re-transmit the device position/orientation data and the patient position/orientation data, respectively, to the medical imaging apparatus 18. In other words, the medical imaging apparatus 18 may track the position and/or the orientation of the mobile electronic device 20 and/or the patient 16 in real-time. Further, the mobile electronic device 20 and/or the patient positional sensor 48 may provide for manual adjustments to the device position/orientation data and the patient position/orientation data, respectively.

By knowing the device position/orientation data and/or the patient position/orientation data, the medical imaging apparatus 18 is able to determine and/or calculate the view of the object 14 within the patient 16 from the perspective of the mobile electronic device 20 along the line of sight 28, and generate the medical images 12 in accordance with such a view. As such, the medical imaging system 18 may generate the medical images 12 such that the medical images 12 may be shown on the display 26 in real-time as the operator 32 moves the mobile electronic device 20 about the patient 16.

Finally, it is also to be understood that the system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the system may include at least one processor and system memory/data storage structures, which may include random access memory (RAM) and read-only memory (ROM). The at least one processor of the system 10 may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium", as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, a system for displaying medical images of an object within a patient is provided. The system includes: a medical imaging apparatus operative to generate the medical images of the object; and a mobile electronic device having a front side and a rear side and operative to electronically communicate with the medical imaging apparatus so as to receive the medical images from the medical imaging apparatus. The front side includes a display, and the rear side is opposite the front side and defines a line of sight that projects outwardly from the mobile electronic device. The mobile electronic device is further operative to move about the patient and show the medical images on the display such that the medical images depict a view of the object from the perspective of the mobile electronic device along the line of sight. In certain embodiments, at least one of the mobile electronic device and the medical imaging apparatus is further operative to broadcast the medical images to a remote electronic device. In certain embodiments, the medical imaging apparatus is at least one of a magnetic resonance imaging device, an ultrasound imaging device, and an x-ray imaging device. In certain embodiments, the medical imaging apparatus is an ultrasound imaging device and the object is a fetus. In certain embodiments, the mobile electronic device transmits at least one of device position data and device orientation data to the medical imaging apparatus, and the medical imaging apparatus generates the medical images based at least in part on at least one of the device position data and the device orientation data. In certain embodiments, the system further includes one or more positioning beacons. In such embodiments, the mobile electronic device is further operative to receive positional reference data from the one or more positioning beacons, and generate the device position data based at least in part on the positional reference data. In certain embodiments, the system further includes a patient positional sensor in electronic communication with the medical imaging apparatus so as to transmit at least one of patient position data and patient orientation data to the medical imaging apparatus. In such embodiments, the medical imaging apparatus generates the medical images based at least in part on at least one of the patient position data and the patient orientation data. In certain embodiments, the rear side of the mobile electronic device includes a camera oriented along the line of sight and operative to generate images of the patient, and the mobile electronic device is further operative to combine the images of the patient with the medical images such that the medical images further depict an augmented reality view of the object and the patient.

Other embodiments provide for a method for displaying medical images of an object within a patient. The method includes: moving a mobile electronic device about the patient, the mobile electronic device having a front side and a rear side opposite the front side, the front side including a display and the rear side defining a line of sight that projects outwardly from the mobile electronic device; generating the medical images via a medical imaging apparatus in electronic communication with the mobile electronic device; transmitting the medical images to the mobile electronic device via the medical imaging apparatus; and displaying the medical images on the mobile electronic device such that the medical images depict a view of the object from the perspective of the mobile electronic device along the line of sight. In certain embodiments the method further includes broadcasting the medical images to a remote electronic device via at least one of the mobile electronic device and the medical imaging apparatus. In certain embodiments, the medical imaging apparatus is at least one of a magnetic resonance imaging device, an ultrasound imaging device, and an x-ray imaging device. In certain embodiments, the medical imaging apparatus is an ultrasound imaging device and the object is a fetus. In certain embodiments, the method further includes transmitting at least one of device position data and device orientation data to the medical imaging apparatus via the mobile electronic device, and wherein generating the medical images via a medical imaging apparatus in electronic communication with the mobile electronic device is based at least in part on at least one of the device position data and the device orientation data. In certain embodiments, the method further includes receiving positional reference data at the mobile electronic device from one or more positioning beacons; and generating the device position data based at least in part on the positional reference data. In certain embodiments, the method further includes transmitting, via a patient positional sensor in electronic communication with the medical imaging apparatus, at least one of patient position data and patient orientation data to the medical imaging apparatus. In such embodiments, generating the medical images via a medical imaging apparatus in electronic communication with the mobile electronic device is based at least in part on at least one of the patient position data and the patient orientation data. In certain embodiments, the method further includes generating images of the patient via a camera disposed on rear side of the mobile electronic device and oriented along the line of sight; and combining the images of the patient with the medial images such that the medical images further depict an augmented reality view of the object and the patient.

Yet still other embodiments provide for a non-transitory computer readable medium. The non-transitory computer readable medium stores instructions configured to adapt a mobile electronic device to: transmit at least one of device position data and device orientation data to a medical imaging apparatus operative to generate medical images of an object within a patient; receive the medical images from the medical imaging apparatus; and show the medical images on a display on a front side of the mobile electronic device such that the medical images depict a view of the object from the perspective of the mobile electronic device along a line of sight extending outwardly from the mobile electronic device from a rear side of the mobile electronic device opposite the front side. In certain embodiments, the stored instructions are further configured to adapt the mobile electronic device to broadcast the medical images to a remote electronic device. In certain embodiments, the stored instructions are further configured to adapt the mobile electronic device to generate images of the patient via a camera disposed on the rear side of the mobile electronic device and oriented along the line of sight; and combine the medical images with the images of the patient such that the medical images further depict an augmented reality view of the object and the patient. In certain embodiments, the medical imaging apparatus is at least one of a magnetic resonance imaging device, an ultrasound imaging device, and an x-ray imaging device.

Accordingly, as will be appreciated, by providing for a mobile electronic device that displays medical images of an object within a patient from the perspective of the mobile electronic device along a line of sight as the mobile electronic device is moved about the patient, some embodiments of the invention provide for a "virtual see-through window" that allows an operator to view an object within the patient. Thus, some embodiments of the invention provide for improved visualization, to include the position and/or orientation with respect to the patient, of a fetus and/or organ by the patient and/or another person, e.g., a physician, medical trainee, friend, and/or relative of the patient.

Further, in medical imaging systems/apparatus wherein the patient is required to remain in a position from which a dedicated monitor/display unit of the medical imaging apparatus is not easily viewed, some embodiments of the invention provide for an improved display from which the patient can view the object. Further, by broadcasting the medical images to a remote electronic device, embodiments of the invention provide for family members and/or remote physicians to view the object within the patient without having to be in the same room as the patient.

Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format are not intended to be interpreted as such, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A system for displaying medical images of an object within a patient comprising:
   a mobile electronic device in communication with a medical imaging apparatus operative to generate the medical images of the object, the mobile electronic device comprising:
   a front side including a display; and
   a rear side opposite the front side and defining a line of sight that projects outwardly from the mobile electronic device,
   wherein the mobile electronic device is operative to:
   transmit at least one of device position data and device orientation data to the medical imaging apparatus;
   receive the medical images from the medical imaging apparatus, wherein the medical images are generated based at least in part on at least one of the device position data and the device orientation data; and
   show the medical images on the display from the perspective of the mobile electronic device along the line of sight such that the display operates as a virtual window to view the object within the patient.

2. The system of claim 1, wherein at least one of the mobile electronic device and the medical imaging apparatus is further operative to broadcast the medical images to a remote electronic device.

3. The system of claim 1, wherein the medical imaging apparatus is at least one of a magnetic resonance imaging device, an ultrasound imaging device, and an x-ray imaging device.

4. The system of claim 1, wherein the medical imaging apparatus is an ultrasound imaging device and the object is a fetus.

5. The system of claim 1, further comprising:
   one or more positioning beacons, and
   wherein the mobile electronic device is further operative to:
   receive positional reference data from the one or more positioning beacons; and
   generate the device position data based at least in part on the positional reference data.

6. The system of claim 1 further comprising:
   a patient positional sensor in electronic communication with the medical imaging apparatus so as to transmit at least one of patient position data and patient orientation data to the medical imaging apparatus, and
   wherein the medical imaging apparatus generates the medical images based at least in part on at least one of the patient position data and the patient orientation data.

7. The system of claim 1, wherein the rear side of the mobile electronic device includes a camera oriented along the line of sight and operative to generate images of the patient, and the mobile electronic device is further operative to combine the images of the patient with the medical images such that the medical images further depict an augmented reality view of the object and the patient.

8. A method for displaying medical images of an object within a patient comprising:

transmitting, by a mobile electronic device, at least one of device position data and device orientation data to a medical imaging apparatus in communication with the mobile electronic device;

receiving, at the mobile electronic device, the medical images from the medical imaging apparatus, wherein the medical images are generated based at least in part on at least one of the device position data and the device orientation data; and displaying, at a display at a front side of the mobile electronic device, the medical images on the mobile electronic device from the perspective of the mobile electronic device along a line of sight extending outwardly from the mobile electronic device from a rear side of the mobile electronic device opposite the front side such that the display operates as a virtual window to view the object within the patient.

9. The method of claim 8 further comprising:

broadcasting the medical images to a remote electronic device via at least one of the mobile electronic device and the medical imaging apparatus.

10. The method of claim 8, wherein the medical imaging apparatus is at least one of a magnetic resonance imaging device, an ultrasound imaging device, and an x-ray imaging device.

11. The method of claim 8, wherein the medical imaging apparatus is an ultrasound imaging device and the object is a fetus.

12. The method of claim 8 further comprising:

receiving positional reference data at the mobile electronic device from one or more positioning beacons; and generating the device position data based at least in part on the positional reference data.

13. The method of claim 8 further comprising:

transmitting, via a patient positional sensor in electronic communication with the medical imaging apparatus, at least one of patient position data and patient orientation data to the medical imaging apparatus; and wherein generating the medical images via a medical imaging apparatus in electronic communication with the mobile electronic device is based at least in part on at least one of the patient position data and the patient orientation data.

14. The method of claim 8 further comprising:

generating images of the patient via a camera disposed on the rear side of the mobile electronic device and oriented along the line of sight; and combining the images of the patient with the medial images such that the medical images further depict an augmented reality view of the object and the patient.

15. A non-transitory computer readable medium storing instructions configured to adapt a mobile electronic device to:

transmit at least one of device position data and device orientation data to a medical imaging apparatus in communication with the mobile electronic device and operative to generate medical images of an object within a patient;

receive the medical images from the medical imaging apparatus, wherein the medical images are generated based at least in part on at least one of the device position data and the device orientation data; and show the medical images on a display on a front side of the mobile electronic device from the perspective of the mobile electronic device along a line of sight extending outwardly from the mobile electronic device from a rear side of the mobile electronic device opposite the front side such that the display operates as a virtual window to view the object within the patient.

16. The non-transitory computer readable medium of claim 15, wherein the stored instructions are further configured to adapt the mobile electronic device to: broadcast the medical images to a remote electronic device.

17. The non-transitory computer readable medium of claim 15, wherein the stored instructions are further configured to adapt the mobile electronic device to:

generate images of the patient via a camera disposed on the rear side of the mobile electronic device and oriented along the line of sight; and combine the medical images with the images of the patient such that the medical images further depict an augmented reality view of the object and the patient.

18. The non-transitory computer readable medium of claim 15, wherein the medical imaging apparatus is at least one of a magnetic resonance imaging device, an ultrasound imaging device, and an x-ray imaging device.

* * * * *